(12) United States Patent
Shimizu et al.

(10) Patent No.: US 10,207,124 B2
(45) Date of Patent: Feb. 19, 2019

(54) LASER LIGHT IRRADIATION DEVICE

(71) Applicant: TERUMO KABUSHIKI KAISHA, Shibuya-ku, Tokyo (JP)

(72) Inventors: Katsuhiko Shimizu, Fujinomiya (JP); Yuuichi Tada, Tokyo (JP); Yuuki Itou, Hadano (JP); Kazuyuki Takahashi, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 542 days.

(21) Appl. No.: 14/868,950

(22) Filed: Sep. 29, 2015

(65) Prior Publication Data
US 2016/0089547 A1 Mar. 31, 2016

(30) Foreign Application Priority Data
Sep. 29, 2014 (JP) .................................. 2014-198763

(51) Int. Cl.
*A61N 5/06* (2006.01)
*G02B 6/26* (2006.01)
(Continued)

(52) U.S. Cl.
CPC .......... *A61N 5/0601* (2013.01); *A61N 5/0625* (2013.01); *G02B 6/00* (2013.01);
(Continued)

(58) Field of Classification Search
CPC .......... A61N 5/0601; A61N 2005/0602; A61N 2005/063; A61N 2005/0665; A61N 2005/067; G02B 6/262; A61B 18/22
(Continued)

(56) References Cited

U.S. PATENT DOCUMENTS 5,428,699 A * 6/1995 Pon .................. A61B 18/24
                                                  385/31
6,302,878 B1 * 10/2001 Daikuzono .......... A61N 5/0601
                                                  606/15
(Continued)

FOREIGN PATENT DOCUMENTS

JP          3406335 B2    5/2003

OTHER PUBLICATIONS

Physics Text Book (Chapter-13) by Boomeria.org web published on Jan. 30, 2009 URL: https://web.archive.org/web/20090130124237/ http://boomeria.org/physicstextbook/ch13.html.*

*Primary Examiner* — Gary Jackson
*Assistant Examiner* — Zahed Kabir
(74) *Attorney, Agent, or Firm* — Buchanan Ingersoll & Rooney PC

(57) ABSTRACT

A laser light irradiation device is disclosed, which can include an optical guide having a columnar portion and transmitting laser light through the columnar portion; a reflecting portion having a reflecting surface that reflects the laser light transmitted through the optical guide; and a transmitting portion having a window part and disposed between the columnar portion of the optical guide and the reflecting portion in such a manner that one end of the transmitting portion is in contact with the columnar portion, the transmitting portion transmitting the laser light emitted from the columnar portion to the reflecting portion and transmitting the laser light reflected by the reflecting surface to cause the laser light to be radiated to an external through the window part. A diameter of the reflecting surface gradually becomes smaller as distance from a boundary between the transmitting portion and the reflecting portion increases.

16 Claims, 6 Drawing Sheets

(51) Int. Cl.
*G02B 6/00* (2006.01)
*A61N 5/067* (2006.01)

(52) U.S. Cl.
CPC ...... *G02B 6/262* (2013.01); *A61N 2005/0602* (2013.01); *A61N 2005/063* (2013.01); *A61N 2005/067* (2013.01); *A61N 2005/0665* (2013.01)

(58) Field of Classification Search
USPC .................................. 607/80, 88–90; 606/16
See application file for complete search history.

(56) References Cited

U.S. PATENT DOCUMENTS

| | | | |
|---|---|---|---|
| 8,882,697 B2* | 11/2014 | Celermajer | A61B 18/1492 604/8 |
| 2007/0106348 A1* | 5/2007 | Laufer | A61B 18/00 607/88 |
| 2009/0287199 A1* | 11/2009 | Hanley | A61B 18/24 606/15 |
| 2014/0107630 A1* | 4/2014 | Yeik | G02B 6/001 606/5 |

\* cited by examiner

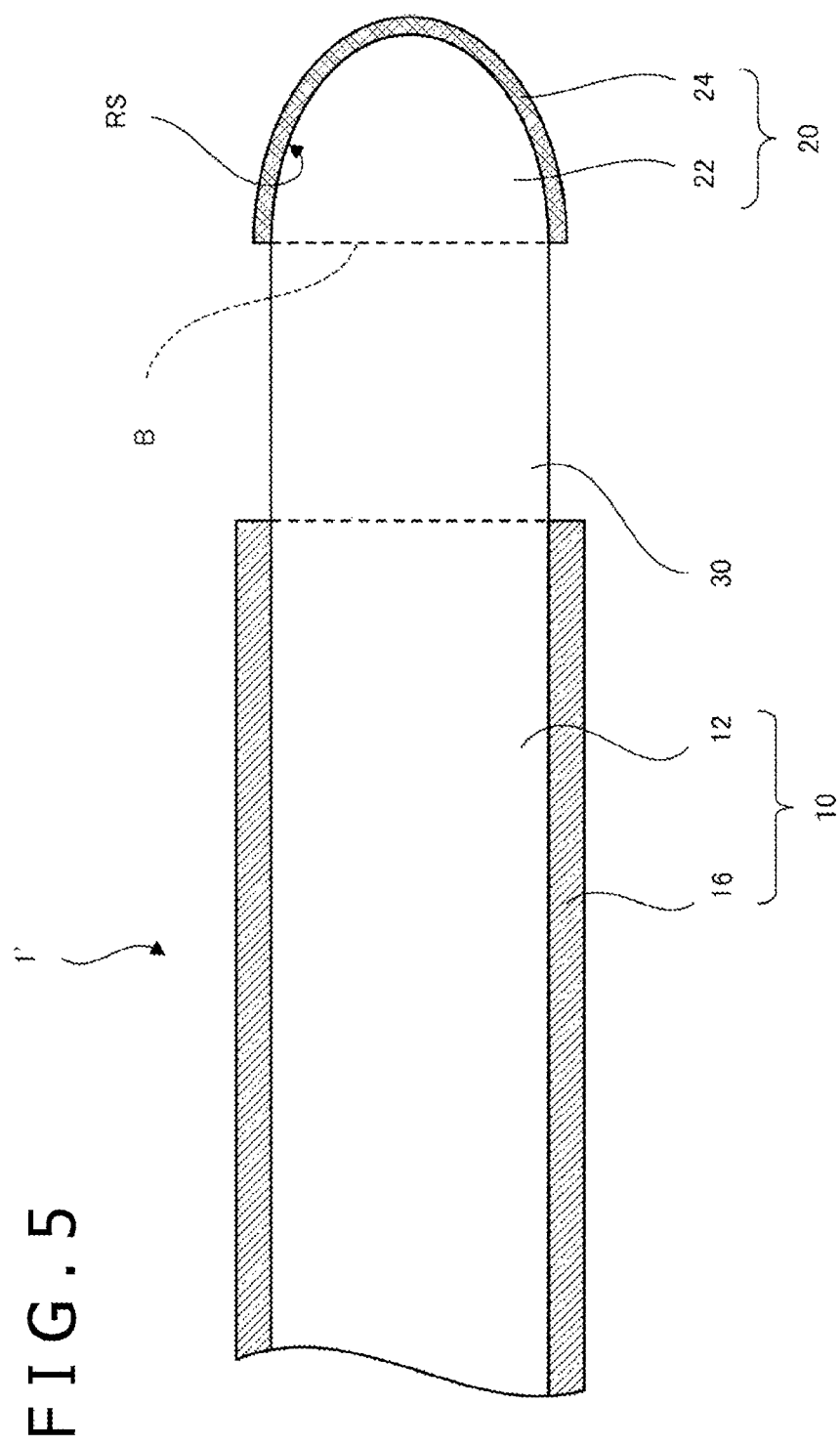

LASER LIGHT IRRADIATION DEVICE

CROSS-REFERENCES TO RELATED APPLICATIONS

This application claims priority to Japanese Patent Application No. 2014-198763 filed on Sep. 29, 2014, the entire content of which is incorporated herein by reference.

TECHNICAL FIELD

The present disclosure generally relates to a laser light irradiation device.

BACKGROUND DISCUSSION

As a treatment method of varicose veins, a method in which a catheter is inserted into a vein and the vein is occluded by irradiating a wall of the vein with laser light through the catheter is known. In Japanese Patent No. 3406335, a laser light irradiation device for medical use in which a transparent sphere is welded to a distal end of an optical fiber and a reflecting film is formed on the surface of the transparent sphere is described. An irradiation window is made in the reflecting film. Light that goes out from the distal end of the optical fiber and enters the inside of the transparent sphere is dispersedly reflected evenly (i.e. reflected a large number of times) by the inner surface of the reflecting film and is radiated to the external through the irradiation window. That is, the transparent sphere with the surface on which the reflecting film is provided functions as an integrator.

In the laser light irradiation device for medical use described in Japanese Patent No. 3406335, the light that has entered the transparent sphere through the optical fiber remains inside the transparent sphere while being reflected a large number of times by the inner surface of the reflecting film. Therefore, the attenuation of the light until radiation of the light to the external through the irradiation window is large. Furthermore, the energy of the light is transduced to heat in this attenuation and the transparent sphere or the optical fiber can be damaged by this heat.

SUMMARY

A laser light irradiation device is disclosed, which can include an optical guide that has a columnar portion and transmits laser light through the columnar portion, a reflecting portion having a reflecting surface that reflects the laser light transmitted through the optical guide, and a transmitting portion that has a window part and is disposed between the columnar portion of the optical guide and the reflecting portion in such a manner that one end of the transmitting portion is in contact with the columnar portion. The transmitting portion transmits the laser light emitted from the columnar portion to the reflecting portion and transmits the laser light reflected by the reflecting surface to cause the laser light to be radiated to the external through the window part. The diameter of the reflecting surface gradually becomes smaller as the distance from the boundary between the transmitting portion and the reflecting portion increases.

A method of treating varicose veins is disclosed, the method comprising: inserting a laser light irradiation device into a vein of a subject, the laser light irradiation device comprising: an optical guide that has a columnar portion and transmits laser light through the columnar portion; a reflecting portion having a reflecting surface that reflects the laser light transmitted through the optical guide; and a transmitting portion that has a window part and is disposed between the columnar portion of the optical guide and the reflecting portion in such a manner that one end of the transmitting portion is in contact with the columnar portion, and wherein a diameter of the reflecting surface gradually becomes smaller as distance from a boundary between the transmitting portion and the reflecting portion increases; and irradiating a wall of the vein by transmitting the laser light emitted from the columnar portion through the transmitting portion to the reflecting portion and wherein the laser light is reflected by the reflecting surface and radiates externally through the window part.

According to the present disclosure, a laser light irradiation device is disclosed that has relatively low loss of the energy of light, relatively low heat generation, and does not readily break.

BRIEF DESCRIPTION OF THE DRAWINGS

FIG. 5 is a schematic sectional view of a laser light irradiation device of another embodiment of the present disclosure.

DETAILED DESCRIPTION

A laser light irradiation device of the present disclosure will be described below through exemplifying embodiments thereof with reference to the accompanying drawings.

Figure 1:
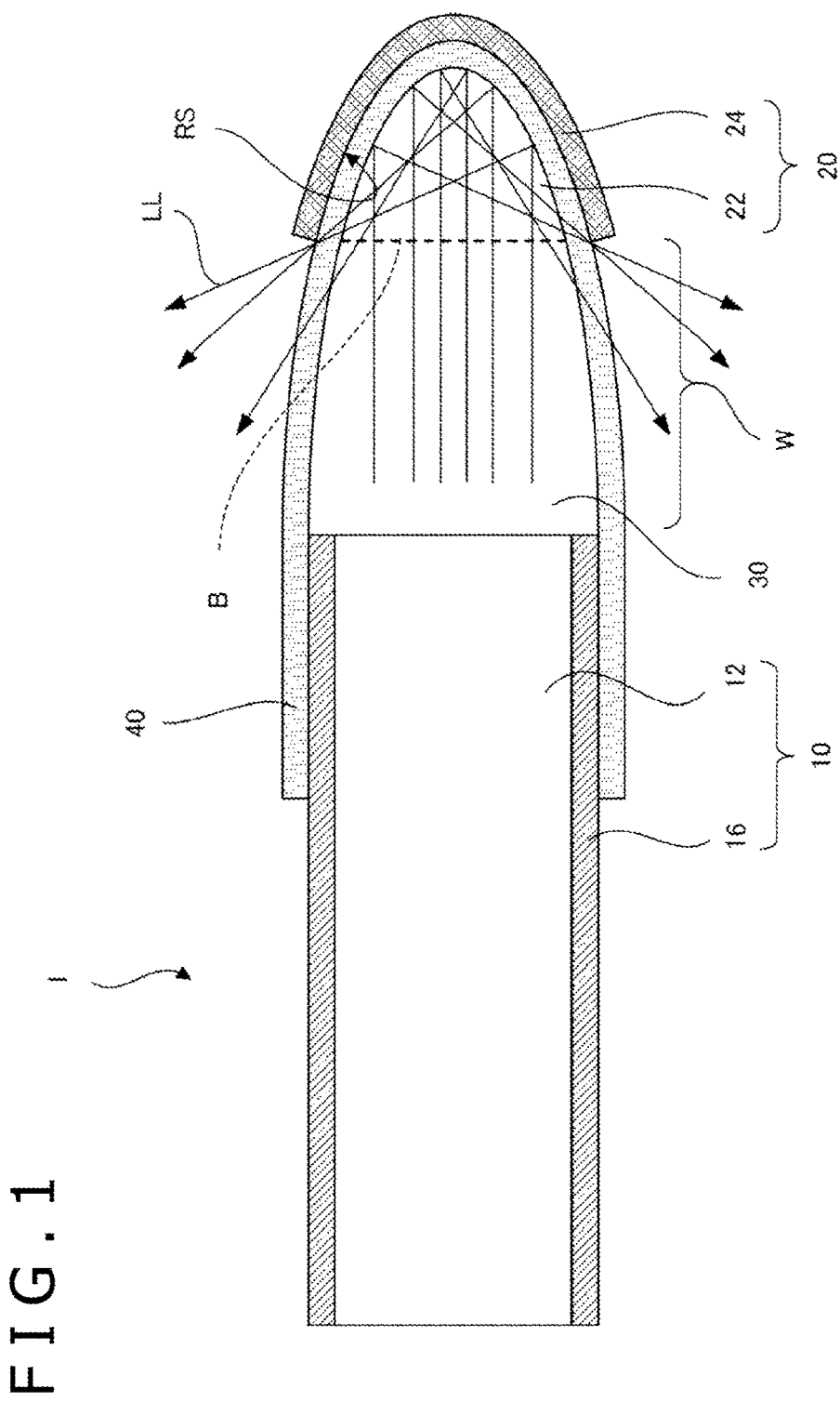
FIG. 1 is a schematic sectional view of a laser light irradiation device of one embodiment of the present disclosure.

FIG. 1 is a schematic sectional view of a laser light irradiation device 1 of one exemplary embodiment of the present disclosure. The laser light irradiation device 1 can be formed as a catheter and can be used for treatment of varicose veins, for example. The laser light irradiation device 1 can include an optical guide 10, a reflecting portion 20, and a transmitting portion 30.

The optical guide 10 has a columnar portion 12 and transmits laser light LL through the columnar portion 12. The columnar portion 12 has a column shape (for example, circular column shape). In accordance with an exemplary embodiment, for example, in the columnar portion 12, the shape of the section orthogonal to the axial direction of the laser light irradiation device 1 or the optical guide 10 can have a constant shape. The optical guide 10 can include a clad 16 disposed around the columnar portion 12. An optical fiber is formed by the columnar portion 12 and the clad 16 disposed around the columnar portion 12 and the columnar portion 12 can function as a core. A reflecting film such as a metal film may be provided as substitute for the clad 16. The optical guide 10 may further have a coating member that coats the clad 16 or the reflecting film.

The reflecting portion 20 has a reflecting surface RS that reflects the laser light LL transmitted through the optical guide 10. The transmitting portion 30 is disposed between the columnar portion 12 of the optical guide 10 and the reflecting portion 20, with one end of the transmitting portion 30 in contact with the columnar portion 12. The transmitting portion 30 has a window part W and transmits the laser light LL emitted from the columnar portion 12 to the reflecting portion 20. In accordance with an exemplary embodiment, the transmitting portion 30 transmits the laser light LL reflected by the reflecting surface RS of the reflecting portion 20 to cause the laser light LL to be radiated to the external through the window part W. When the laser light irradiation device 1 is used for treatment of varicose veins, a wall of a vein is irradiated with the laser light LL radiated to the external through the window part W and thereby the vein is occluded. In accordance with an exemplary embodiment, the diameter of the reflecting surface RS gradually becomes smaller as the distance from a boundary B between the transmitting portion 30 and the reflecting portion 20 (portion having the reflecting surface RS) increases. Here, the diameter of the reflecting surface RS means the diameter of a section obtained by cutting the reflecting surface RS by a plane orthogonal to the axial direction of the laser light irradiation device 1 (x-axis direction).

According to the above configuration, the laser light LL that enters the reflecting portion 20 through the optical guide 10 goes to the external through the window part W with a small number of times of reflection. Thus, loss of the energy or heat generation in the reflecting portion 20 or the transmitting portion 30 can be reduced and the irradiation efficiency of the laser light can be improved. Furthermore, the laser light irradiation device 1 is less readily broken.

In accordance with an exemplary embodiment, it can be preferable that the ratio of the laser light LL that is reflected by the reflecting portion 20 only once and goes to the external through the transmitting portion 30 relative to the whole of the laser light LL that enters the reflecting portion 20 through the optical guide 10 is equal to or higher than 70%. In addition, it can be more preferable that the ratio is equal to or higher than 80% and it is ideal that the ratio is equal to or higher than 90%. Thus, the reflecting portion 20 can be designed to satisfy the above-described ratio. Here, the above-described ratio is determined by the shape of the reflecting surface RS.

The reflecting portion 20 can include an optically transmissive portion 22 in contact with the other end of the transmitting portion 30 and a reflecting film 24 that is disposed outside the optically transmissive portion 22 and forms the reflecting surface RS. The laser light irradiation device 1 can include a cap 40 that surrounds at least part of the optical guide 10, the transmitting portion 30, and the optically transmissive portion 22. In this case, the reflecting film 24 can be disposed outside the cap 40 to cover the optically transmissive portion 22 for example, and the reflecting surface RS can be formed by the boundary between the reflecting film 24 and the cap 40. The reflecting film 24 can be formed by evaporating a metal onto the surface of the cap 40, for example. The transmitting portion 30 and the optically transmissive portion 22 can be formed of a liquid or a gas. In this case, the boundary B between the transmitting portion 30 and the optically transmissive portion 22 is not a boundary as a physical interface but a virtual boundary.

Figure 2A:
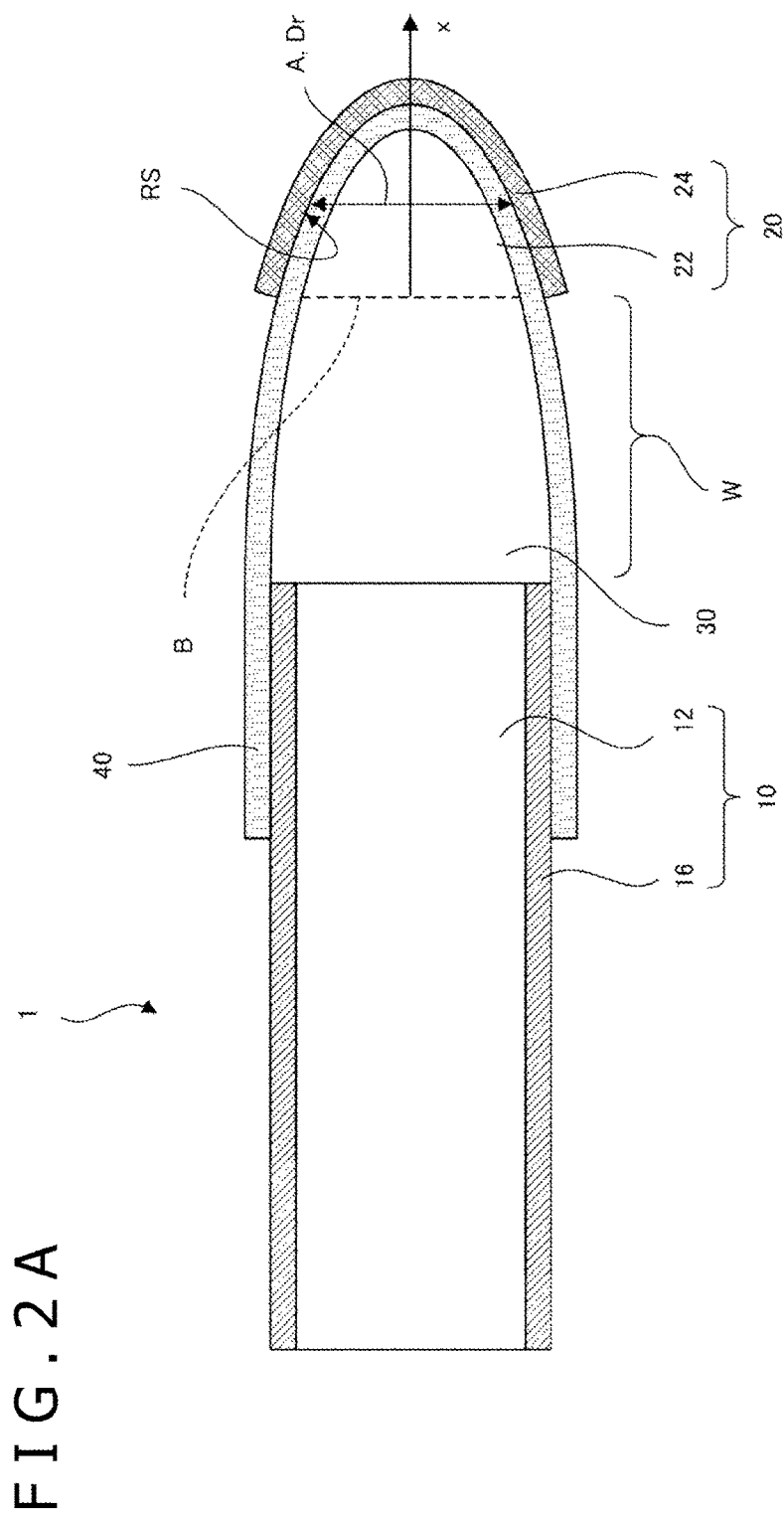
FIGS. 2A to 2C are diagrams exemplifying the configuration of a reflecting surface of the laser light irradiation device of the one embodiment of the present disclosure.

The shape of the reflecting surface RS will be described in an exemplifying manner with reference to FIG. 2A. The x-axis in FIG. 2A is parallel to the axial direction of the laser light irradiation device 1. The axial direction of the laser light irradiation device 1 corresponds with the axial direction of the optical guide 10. The reflecting surface RS can have a taper part. In accordance with an exemplary embodiment, the reflecting surface RS can have various shapes. For example, the reflecting surface RS can be a spherical surface or a parabolic surface. If, for example, the reflecting surface RS is formed of a spherical surface or a parabolic surface, laser light that is emitted from the optical guide 10 along the axial direction to be incident on the reflecting surface RS and be reflected by the reflecting surface RS passes through the focal point of the spherical surface or the parabolic surface and is radiated from the window part W to the external. The focal point of the spherical surface exists at a position of $x=r/2$ when the radius of this spherical surface is defined as r.

Figure 2B:
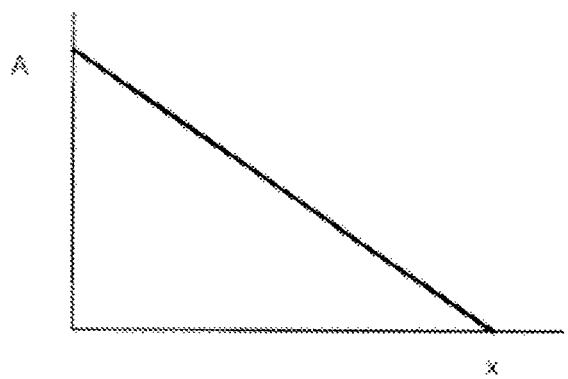
Figure 2C:
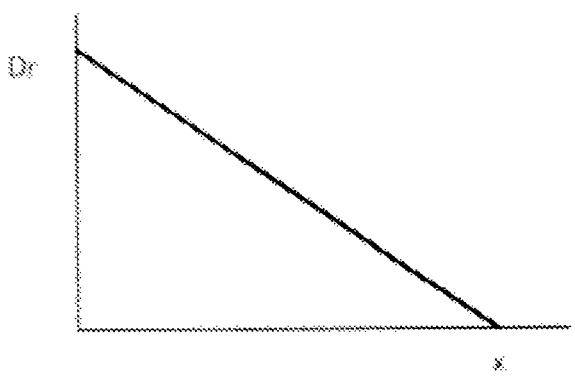

In accordance with an exemplary embodiment, the reflecting surface RS can include a part in which a sectional area A becomes smaller linearly as the distance from the boundary B between the transmitting portion 30 and the reflecting portion 20 increases as exemplified in FIG. 2B. Here, the sectional area A means the area of the inside of a section obtained by cutting the reflecting surface RS by a plane orthogonal to the axial direction of the laser light irradiation device 1 (x-axis direction). Alternatively, the reflecting surface RS can include a part in which a diameter Dr becomes smaller linearly as the distance from the boundary B between the transmitting portion 30 and the reflecting portion 20 increases as exemplified in FIG. 2C. The configuration of the reflecting surface RS exemplified here provides a structure in which the diameter of the distal side of the reflecting surface RS is set smaller, which can be advantageous for increasing the width of the laser light radiated to the external through the window part W in the x-direction.

The transmitting portion 30 can be formed to have a taper part, for example, in such a manner that its diameter gradually becomes smaller as the distance from the columnar portion 12 of the optical guide 10 increases. Alternatively, the transmitting portion 30 can have a column shape with a constant diameter.

Figure 3:
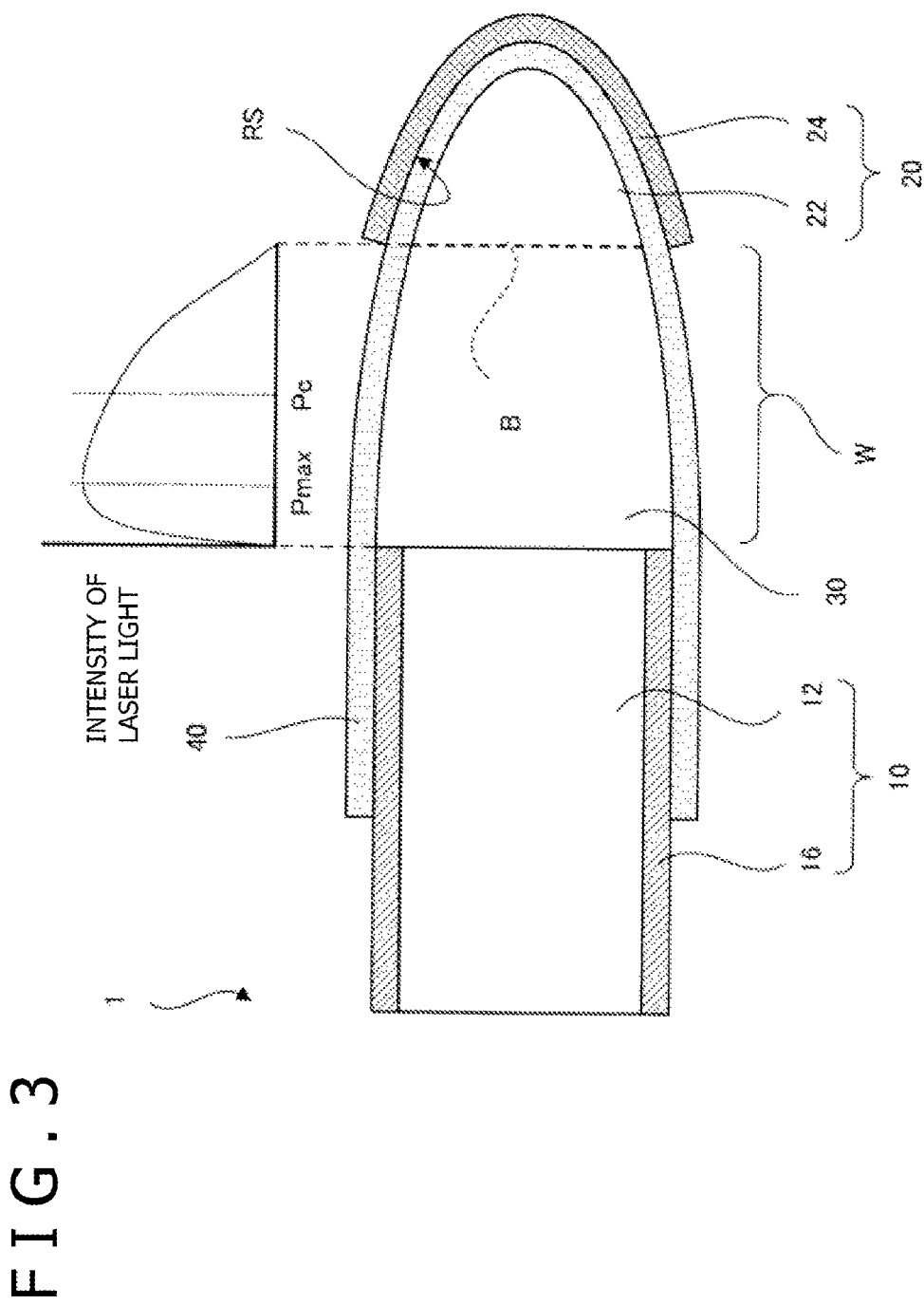
FIG. 3 is a diagram for explaining a preferable structure of the laser light irradiation device of the one embodiment of the present disclosure.

In FIG. 3, in accordance with an exemplary embodiment, preferable distribution of the intensity of the laser light radiated from the window part W is exemplified. As exemplified in FIG. 3, it can be preferable that, in the intensity distribution of the laser light radiated from the window part W in the axial direction of the laser light irradiation device 1, a position Pmax at which the maximum intensity is indicated is closer to the optical guide 10 than the center Pc of the transmitting portion 30 in this axial direction. Such intensity distribution can be advantageous for suppressing a further excess temperature rise after the temperature of the respective parts of a wall of a vein has reached a target temperature and keeping the temperature during a predetermined time in a procedure of irradiating the wall of the vein with laser light while moving the laser light irradiation device 1 in such a direction as to draw out the laser light irradiation device 1 from the blood vessel. Conversely, when the position Pmax at which the maximum intensity is indicated is closer to the reflecting portion 20 than the center Pc of the transmitting portion 30 in the axial direction, a further excess temperature rise can occur after the temperature has reached the target temperature at the respective parts of the wall of the vein. If this temperature rise becomes too excessive, the wall of the vein can be broken. The intensity distribution in which the position Pmax at which the maximum intensity is indicated is closer to the optical guide 10 than the center Pc of the transmitting portion 30 in the axial direction can be obtained by forming the reflecting surface RS by a spherical surface or a parabolic surface as described above for example. Here, in the laser light passing through the optical fiber as the optical guide 10, the intensity at the central part is the highest, which can be advantageous in the configuration of the above-described intensity distribution.

In accordance with an exemplary embodiment, the intensity distribution in which the position Pmax at which the maximum intensity is indicated is closer to the optical guide 10 than the center Pc of the transmitting portion 30 in the axial direction can be obtained by making a configuration in which the reflectance of the reflecting surface RS is the highest at the central part of the reflecting surface RS. In accordance with an exemplary embodiment, this can be because at the central part of the reflecting surface RS, the angle difference from the plane orthogonal to the axial direction of the laser light irradiation device 1 is small. Therefore, as exemplified in FIG. 1, laser light reflected at the central part travels at a smaller angle to the axial direction than laser light reflected at the peripheral part.

Figure 4:
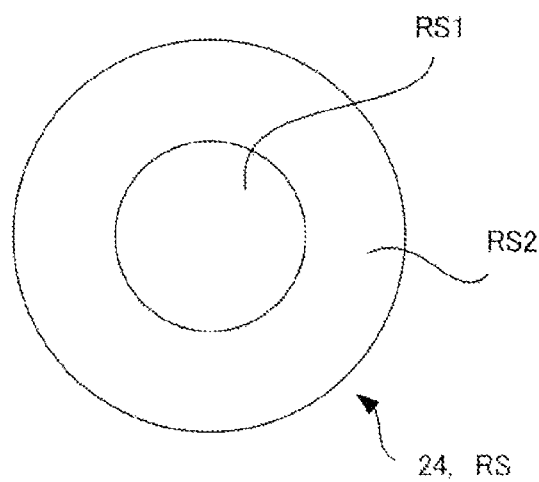
FIG. 4 is a diagram exemplifying the configuration of the reflecting surface of the laser light irradiation device of the one embodiment of the present disclosure.

In FIG. 4, a configuration example for setting the reflectance of the reflecting surface RS highest at the central part of the reflecting surface RS is shown. In the example shown in FIG. 4, the reflecting surface RS has a central part RS1 and a peripheral part RS2 surrounding the central part RS1. The reflectance of the central part RS1 is higher than that of the peripheral part RS2. The central part RS1 can be formed of, for example, silver and the peripheral part RS2 can be formed of, for example, aluminum, copper, gold, or platinum. Although the reflecting surface RS is composed of two regions (central part RS1 and peripheral part RS2) different from each other in the reflectance in the example shown in FIG. 4, the reflecting surface RS may be composed of three or more regions different from each other in the reflectance. In this case, the reflectance of each region can be so decided that the reflectance becomes lower in a stepwise manner from the central part toward the outside. The reflecting surface RS may be so configured that the reflectance gradually decreases from the central part toward the outside.

In FIG. 5, a laser light irradiation device 1' of another embodiment is shown. A columnar portion 12 of an optical guide 10, a transmitting portion 30, and an optically transmissive portion 22 of a reflecting portion 20 can be formed by the same material as members having a continuous monolithic structure. A reflecting film 24 can be formed on the surface of the optically transmissive portion 22, for example, by evaporation. The laser light irradiation device 1' can be manufactured by the following method. First, with application of tension of an optical fiber, part of the optical fiber is heated to fuse a core and a clad of the optical fiber to each other. Then, the tension is weakened at a timing when the temperature of the heated part surpasses, for example, 1000° C. and the optical fiber begins to extend, and cutting of the optical fiber at the heated part is awaited. Subsequently, the distal part of the cut optical fiber is heated again to round the distal part. Through the above steps, a member having the optically transmissive portion 22 in which a sectional area A linearly changes as shown in FIG. 2B and the optical guide 10 can be obtained. Subsequently, the reflecting film 24 is formed by evaporating a metal (for example, silver) onto the surface of the optically transmissive portion 22.

The detailed description above describes a laser light irradiation device. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A laser light irradiation device comprising:
    an optical guide having a columnar portion and configured to transmit laser light through the columnar portion;
    a reflecting portion having a reflecting surface configured to reflect the laser light transmitted through the optical guide, the reflecting portion including an optically transmissive portion through which light is transmitted and a reflecting film disposed outside the optically transmissive portion;
    a transmitting portion having a window part, the transmitting portion being disposed between the columnar portion of the optical guide and the reflecting portion in such a manner that one end of the transmitting portion is in contact with the columnar portion, the transmitting portion configured to transmit the laser light emitted from the columnar portion to the reflecting portion and to transmit the laser light reflected by the reflecting surface to cause the laser light to be radiated externally through the window part;
    a cap configured to surround at least part of the columnar portion, the transmitting portion, and the optically transmissive portion, the reflecting film being disposed outside the cap to cover the optically transmissive portion, and the reflecting surface being formed by a boundary between the reflecting film and the cap; and
    wherein a diameter of the reflecting surface gradually becomes smaller as a distance from a boundary between the transmitting portion and the reflecting portion increases, and a diameter of the transmitting portion becomes smaller as a distance from the columnar portion increases.

2. The laser light irradiation device according to claim 1, wherein in intensity distribution of the laser light radiated from the window part in an axial direction of the laser light irradiation device, a position at which maximum intensity is indicated is closer to the optical guide than a center of the transmitting portion in the axial direction.

3. The laser light irradiation device according to claim 1, wherein reflectance of the reflecting surface is highest at a central part of the reflecting surface.

4. The laser light irradiation device according to claim 3, wherein the reflecting surface has a plurality of regions different from each other in the reflectance.

5. The laser light irradiation device according to claim 1, wherein the reflecting surface has a focal point and the laser light reflected by the reflecting surface passes through the focal point and is radiated to the external.

6. The laser light irradiation device according to claim 5, wherein the reflecting surface is a spherical surface.

7. The laser light irradiation device according to claim 5, wherein the reflecting surface is a parabolic surface.

8. The laser light irradiation device according to claim 1, wherein the columnar portion of the optical guide, the transmitting portion, and an optically transmissive portion of the reflecting portion are formed of a same material and having a continuous monolithic structure.

9. A method of treating varicose veins, the method comprising:
    inserting a laser light irradiation device into a vein of a subject, the laser light irradiation device comprising:
        an optical guide having a columnar portion and configured to transmit laser light through the columnar portion;

a reflecting portion having a reflecting surface configured to reflect the laser light transmitted through the optical guide, the reflecting portion including an optically transmissive portion through which light is transmitted and a reflecting film disposed outside the optically transmissive portion;

a transmitting portion having a window part, the transmitting portion being and is disposed between the columnar portion of the optical guide and the reflecting portion in such a manner that one end of the transmitting portion is in contact with the columnar portion, the transmitting portion configured to transmit the laser light emitted from the columnar portion to the reflecting portion and to transmit the laser light reflected by the reflecting surface to cause the laser light to be radiated externally through the window part;

a cap configured to surround at least part of the columnar portion, the transmitting portion, and the optically transmissive portion, the reflecting film being disposed outside the cap to cover the optically transmissive portion, and the reflecting surface being formed by a boundary between the reflecting film and the cap; and wherein a diameter of the reflecting surface becomes smaller as a distance from a boundary between the transmitting portion and the reflecting portion increases, and a diameter of the transmitting portion becomes smaller as a distance from the columnar portion increases; and irradiating a wall of the vein by transmitting the laser light emitted from the columnar portion through the transmitting portion to the reflecting portion and wherein the laser light is reflected by the reflecting surface and radiates externally through the window part.

10. The method according to claim 9, comprising:
occluding the vein with the laser light radiating externally through the window part.

11. The method according to claim 9, wherein in intensity distribution of the laser light radiated from the window part in an axial direction of the laser light irradiation device, a position at which maximum intensity is indicated is closer to the optical guide than a center of the transmitting portion in the axial direction.

12. A laser light irradiation device, the laser light irradiation device comprising:

an optical guide having a columnar portion, the optical guide being configured to transmit laser light through the columnar portion;

a reflecting portion having a reflecting surface configured to reflect the laser light transmitted through the optical guide;

a transmitting portion having a window part, the transmitting portion being disposed between the columnar portion of the optical guide and the reflecting portion in such a manner that one end of the transmitting portion is in contact with the columnar portion, the transmitting portion configured to transmit the laser light emitted from the columnar portion to the reflecting portion and to transmit the laser light reflected by the reflecting surface to cause the laser light to be radiated externally through the window part, and wherein a diameter of the reflecting surface becomes smaller as a distance from a boundary between the transmitting portion and the reflecting portion increases; and wherein the reflecting portion includes an optically transmissive portion through which light is transmitted and a reflecting film disposed outside the optically transmissive portion, and a cap configured to surrounds at least part of the columnar portion, the transmitting portion, and the optically transmissive portion, the reflecting film being disposed outside the cap to cover the optically transmissive portion, and the reflecting surface being formed by a boundary between the reflecting film and the cap.

13. The laser light irradiation device according to claim 12, wherein in intensity distribution of the laser light radiated from the window part in an axial direction of the laser light irradiation device, a position at which maximum intensity is indicated is closer to the optical guide than a center of the transmitting portion in the axial direction.

14. The laser light irradiation device according to claim 12, wherein reflectance of the reflecting surface is highest at a central part of the reflecting surface.

15. The laser light irradiation device according to claim 14, wherein the reflecting surface has a plurality of regions different from each other in the reflectance.

16. The laser light irradiation device according to claim 12, wherein the columnar portion of the optical guide, the transmitting portion, and an optically transmissive portion of the reflecting portion are formed of a same material and having a continuous monolithic structure.

* * * * *